United States Patent
Maurel et al.

(10) Patent No.: US 7,208,603 B2
(45) Date of Patent: Apr. 24, 2007

(54) SYNTHESIS METHOD AND INTERMEDIATES OF PYRIDIN-2-YL-METHYLAMINE

(75) Inventors: Jean-Louis Maurel, Castres (FR); Bernard Bonnaud, Lagarrigue (FR); Jean-Paul Ribet, Mazamet (FR); Bernard Vacher, Castres (FR)

(73) Assignee: Pierre Fabre Medicament, Boulogne Billancourt (FR)

( * ) Notice: Subject to any disclaimer, the term of this patent is extended or adjusted under 35 U.S.C. 154(b) by 550 days.

(21) Appl. No.: 10/467,467

(22) PCT Filed: Feb. 11, 2002

(86) PCT No.: PCT/FR02/00508

§ 371 (c)(1),
(2), (4) Date: Jan. 27, 2004

(87) PCT Pub. No.: WO02/064585

PCT Pub. Date: Aug. 22, 2002

(65) Prior Publication Data

US 2004/0116705 A1    Jun. 17, 2004

(30) Foreign Application Priority Data

Feb. 9, 2001    (FR) .................................. 01 01784

(51) Int. Cl.
*C07D 401/12* (2006.01)

(52) U.S. Cl. ....................................................... 546/194

(58) Field of Classification Search ................. 546/194
See application file for complete search history.

(56) References Cited

U.S. PATENT DOCUMENTS

| 4,482,437 A | 11/1984 | Toomey, Jr. ................. 204/74 |
| 6,020,345 A * | 2/2000 | Vacher et al. ............... 514/318 |

FOREIGN PATENT DOCUMENTS

| WO | WO97/24122 | 7/1997 |
| WO | WO98/02442 | 1/1998 |
| WO | WO98/22459 | 5/1998 |

OTHER PUBLICATIONS

Vacher et al. "Novel derivatives of 2-pyridinemethylamine . . . " J. Med. Chem. 42, p. 1648-1660 (1999).*
Davies, L.S. et al, "Quinolizins. Part XIII. Rearrangement of Quinolizinium-I-diazonium Salts into v-Triazolo[1,5-a]pyridines," J. Chem. Soc. (C), 1970, pp. 688-693.
Zheng, H. et al, "Complexes with $Fe^{III}_2(\mu-O)(\mu-OH)$, with $Fe^{III}_2(\mu-O)_2$ and $[Fe^{III}_3(\mu_2-O_3)]$ Cores: Structures, Spectroscopy, and Core Interconversions," J. Am. Chem. Soc. 121, 1999, pp. 2226-2235.
Ayi A.I. et al, "Nouvelle Voie de Synthese d'Acides Amines Monofluores," Tetrahedron Letters, vol. 22, No. 16, 1981, pp. 1505-1508.
Minor et al, "Synthesis of 2- and 6-Fluoronicotinamides," J. Am. Chem. Soc., vol. 71, 1949, pp. 4152-4153.

* cited by examiner

*Primary Examiner*—Celia Chang
(74) *Attorney, Agent, or Firm*—Steptoe & Johnson LLP

(57) ABSTRACT

The invention concerns a novel method for preparing pyridin-2-yl-methylamine derivatives by reducing amination of cyanohydrins.

11 Claims, No Drawings

SYNTHESIS METHOD AND INTERMEDIATES OF PYRIDIN-2-YL-METHYLAMINE

The present invention relates to a novel method for preparing pyridin-2-yl-methylamine derivatives of formula (I):

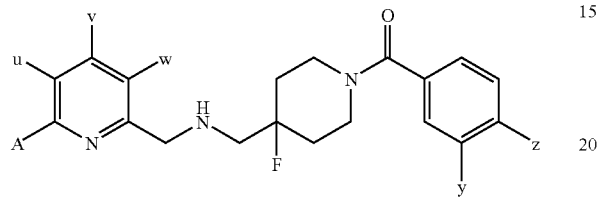

(I)

in which:

u represents a hydrogen atom or a methyl radical;

v represents a hydrogen atom or a chlorine atom or a methyl radical;

w represents a hydrogen atom or a fluorine atom or a methyl radical;

y represents a chlorine atom or a methyl radical;

z represents a hydrogen atom or a fluorine atom or a chlorine atom or a methyl radical; and A represents:
- a hydrogen atom or a fluorine atom or a chlorine atom;
- a $C_1$–$C_5$ alkyl radical;
- a fluoroalkyl radical;
- a cyclopropyl radical;
- a 5-membered aromatic heterocyclic group;
- an alkoxy or alkylthio group;
- a cyclic amino group;
- an alkoxycarbonyl group; or
- an amino group of the type:

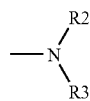

in which R2 or R3, which are identical or different, represent hydrogen, or a $C_1$–$C_5$ alkyl radical as defined above or a cyclopropyl or cyclobutyl radical or a trifluoromethyl radical.

The method is characterized by the reaction of a cyanohydrin of formula (III):

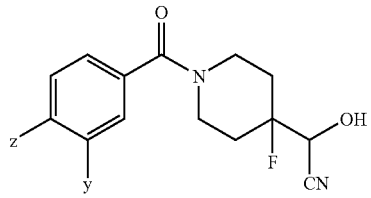

(III)

and of a pyridin-2-yl-methylamine of formula (IV):

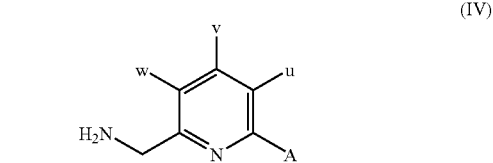

(IV)

According to a particular embodiment of the invention, the reaction medium may, in some cases, be advantageously made basic by the addition of an organic base of the tertiary amine type. 1,4-Diaza-bicyclo[2.2.2]octane will be used in particular.

According to another characteristic embodiment of the method of the invention, the reaction medium is made reducing by the addition of a simple or complex boron hydride, in particular sodium cyanoborohydride.

According to an additional characteristic of the present invention, such a method will be advantageously carried out in a reaction medium of the alcohol type, in particular in a methanolic medium.

According to another additional characteristic of the method of the invention, the primary amine, a starting reagent of formula (IV), may be used in the form of a hydrochloride, this being more particularly so in the case of the preparation of a pyridin-2-yl-methylamine.

These compounds are useful as medicaments, in particular as antidepressants and analgesics.

In the prior art, illustrated in WO 9822459, the compounds of formula (I) are obtained from a 1-benzoyl-piperidin-4-one (formula II). The ketone functional group of the compounds of formula (II) is converted to an epoxide (IIa), which, when treated with an excess of the hydrogen fluoride-pyridine complex, leads to a 1-benzoyl-4-fluoro-4-hydroxymethylpiperidine (IIb). The primary alcohol functional group of this compound (IIb) is then activated in the form of an ester of para-toluenesulfonic acid (IIc) to give, after reaction with potassium phthalimide, a 1-benzoyl-4-fluoro-4-(1-phthalimidoylmethyl)piperidine (IId). This inter-mediate, after treating with ethanolamine, gives a 1-benzoyl-4-fluoro-4-aminomethylpiperidine (IIe), which is then used in a reductive amination reaction with an appropriate aldehyde to give the compounds of formula (I).

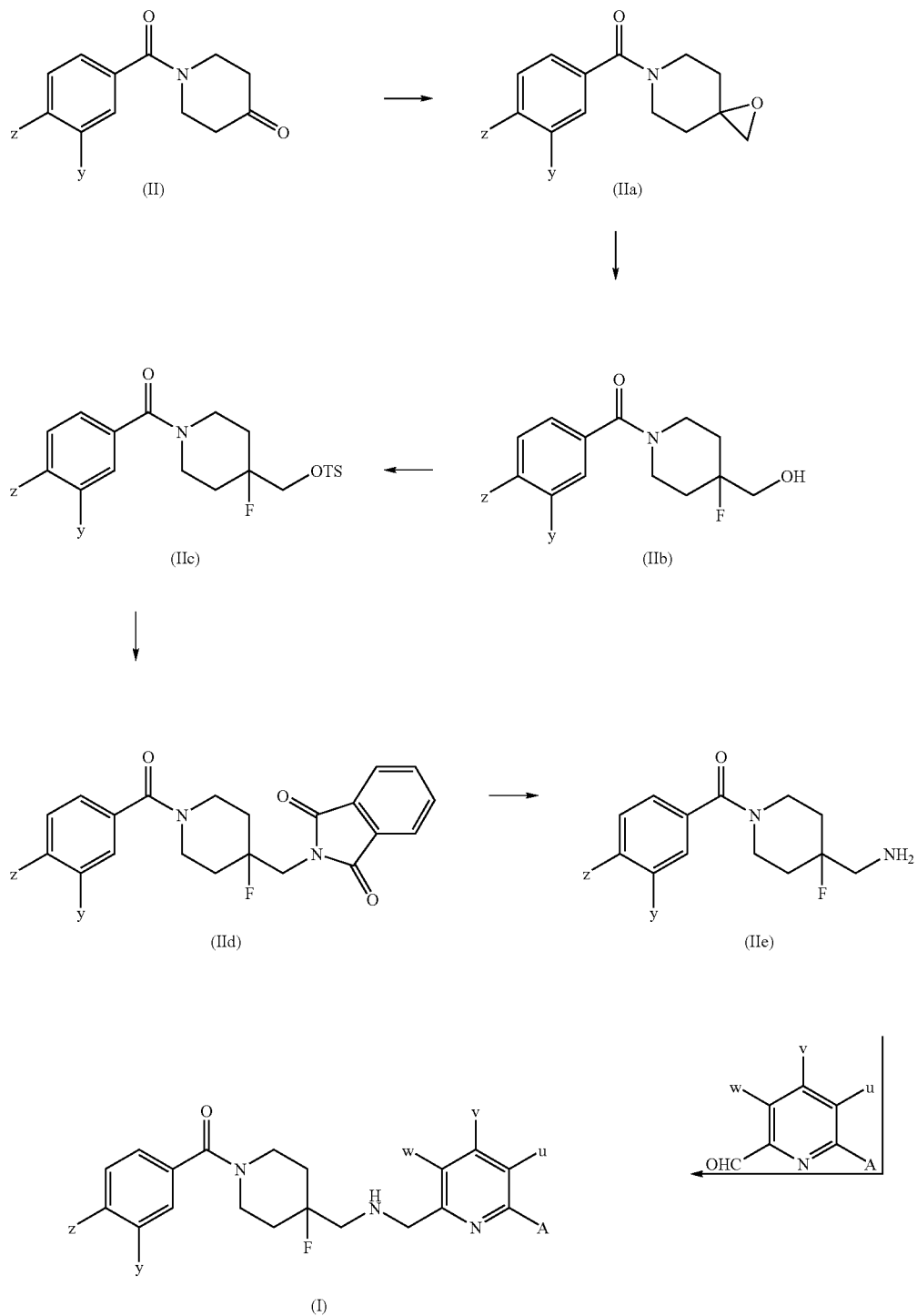

(Scheme I)

The production of compounds of formula (I) according to the method, as described in WO 9822459, requires 6 steps starting with the intermediate of formula (II) and gives a mean optimized overall yield of 5%.

The present method, which uses a new reductive amination reaction between a cyanohydrin (formula III) and a pyridin-2-yl-methylamine (formula IV), advantageously replaces the previous method.

The method using this novel reaction is described in scheme II:

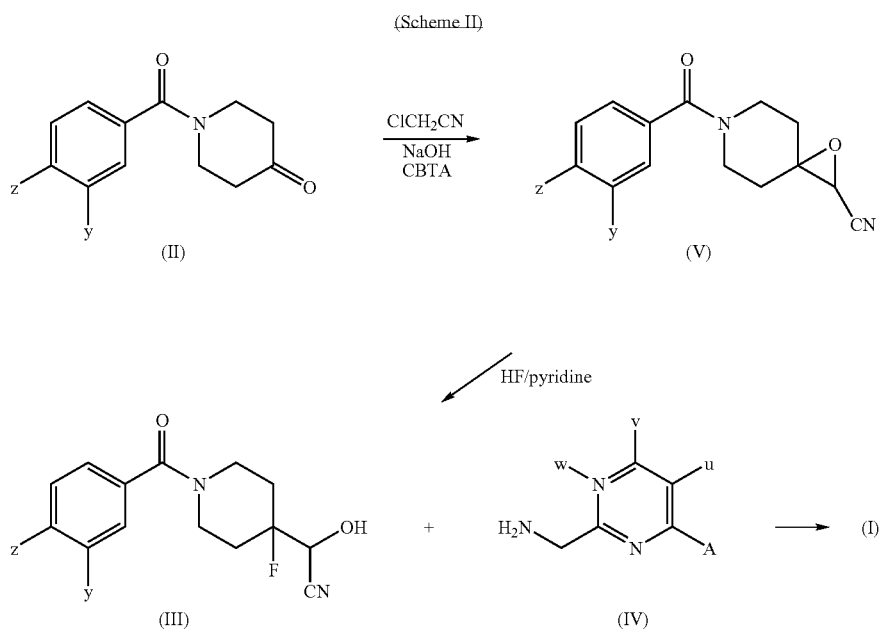

A Darzens reaction between benzoylpiperidin-4-ones (II) and an acetonitrile halide (A. Jonczyk, Tetrahedron Lett. (1972), 23, 2395–96) gives the corresponding cyanoepoxides (formula V). This reaction is advantageously carried out according to a phase transfer technique under the operating conditions developed by the inventors. The opening of the epoxide (V) by means of hydrofluoric acid or other fluorinating agents, according to the techniques described for example in:

J. Fluorine Chem. (1999), 99(2), 95–97
Yuki Gosei Kagaku Kyokaishi (1998), 56(4), 312–319
J. Fluorine Chem. (1995), 70(1), 1–3
J. Fluorine Chem. (1995), 70(1), 141–4
Tetrahedron Lett. (1990), 31(49), 7209–12
J. Chem. Soc., Chem. Commun. (1989), (23), 1848–50 gives the cyanohydrins of formula (III). The latter are then reacted with the pyridin-2-yl-methylamines (formula IV) or their salt, in a reducing and optionally basic medium in order to directly give the compounds of formula (I). The average overall yield of this method, starting with the intermediate of formula (II) is 23%, which represents a gain in productivity of 450% compared with the initial method (scheme I).

The yields of this new reaction, applied to the cyanohydrin (III), (scheme II), and the primary amine (IV), and the purity of the products obtained, therefore allow a more economical and effective industrial synthesis.

The reductive amination reaction is advantageously carried out at room temperature.

When the pyridin-2-yl-methylamines are in salt form, then the reaction medium is advantageously made basic by means of an organic base, of the tertiary amine type, such as for example 1,4-diazabicyclo[2.2.2]octane (DABCO).

The reducing medium is advantageously obtained by means of a simple or complex boron hydride, or a mixture of boron hydrides, and in particular sodium cyanoborohydride ($NaBH_3CN$).

In some cases, in particular when (6-aminomethyl-5-methyl-pyridin-2-yl)methylamine (formula IVb) is used, a by-product of formula (VII) appears, (scheme III).

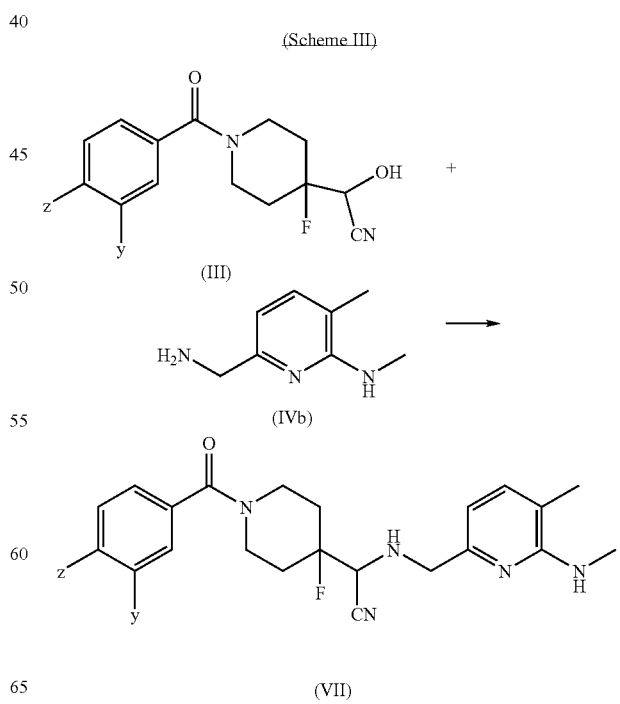

This side reaction can be eliminated by adding iron sulfate (FeSO$_4$.7H$_2$O) to the reaction medium. Other metal salts capable of completing the cyanide ions can also be used in the reductive amination reaction in question.

The preparation of the (5-methyl-pyridin-2-yl)methylamine (formula IVa) used in this method is described in EP 718 300 or U.S. Pat. No. 4,482,437.

The preparation of (6-aminomethyl-5-methylpyridin-2-yl)methylamine (formula IVb), is described below and was carried out according to the sequence of reactions represented in scheme IV.

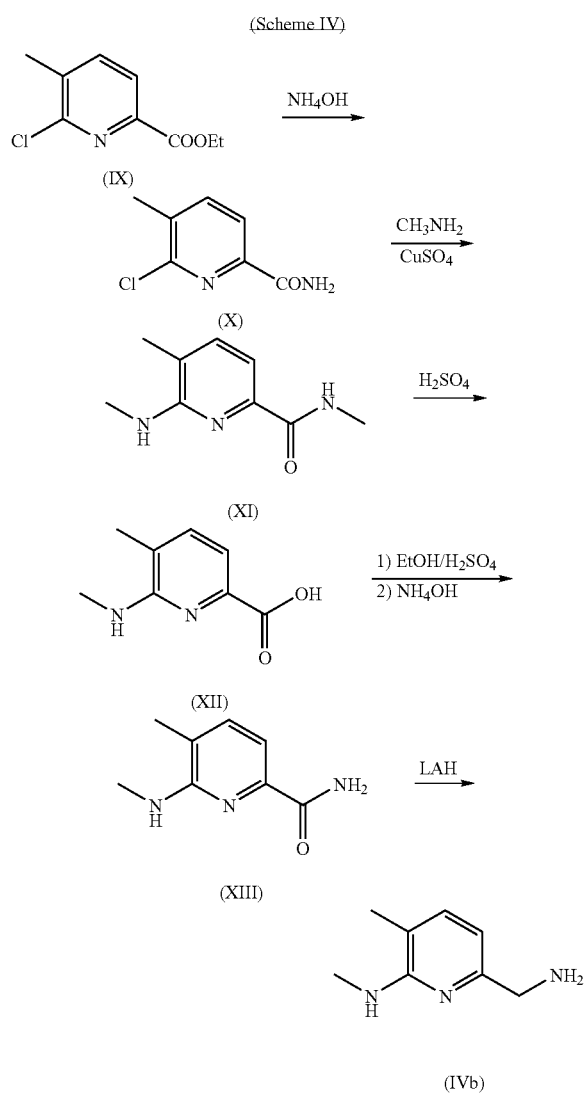

The preparation of 2-ethoxycarbonyl-5-methyl-6-chlorpyridine (compound IX) is described in WO 9822459. This intermediate, when treated with aqueous ammonia, gives the 2-carboxamido-5-methyl-6-chloropyridine derivative (formula X) which reacts in the hot state and under pressure with methylamine in the presence of copper sulfate to give 2-N-methylamido-5-methyl-6-methylaminopyridine (formula XI). Acid hydrolysis of the amide, followed by esterification and treatment with aqueous ammonia gives 2-carboxamido-5-methyl-6-methylaminopyridine (formula XIII) which is reduced to (6-aminomethyl-5-methylpyridin-2-yl) methylamine (formula IVb) by means of lithium aluminum hydride.

The following examples illustrate the invention without however limiting the scope thereof.

EXAMPLE 1

(6-Aminomethyl-5-methylpyridin-2-yl)-methylamine (IVb)

Step 1: 2-Carboxamido-5-methyl-6-chloropyridine (IX).

Dissolve 26 g of 2-ethoxycarbonyl-5-methyl-6-chloropyridine (crude oil containing about 60% of ester) in 130 ml of methanol. Add 200 ml of 32% aqueous ammonia and stir overnight at room temperature. The product is recovered by filtration and gives, after washing with water and drying under vacuum, 13 g of white crystals. m.p.=146° C.

Step 2: 2-Methylcarboxamido-5-methyl-6-methylamino-pyridine (XI).

73 g of 2-carboxamide-5-methyl-6-chloropyridine and 200 ml of methylamine at 40% in ethanol, 110 ml of methylamine at 40% in water and 34 g of anhydrous copper sulfate are introduced into a sealed stainless steel reactor. The reactor is then closed and heated, with stirring, for 24 hours at 110° C. After cooling, the reaction medium is diluted with 300 ml of water and aqueous ammonia at 32%. The product is extracted twice with dichloromethane and then washed with salt water. After drying and evaporation, 52.4 g of white crystals are recovered. m.p.=158° C.

Step 3: 5-Methyl-6-methylaminopyridine-2-carboxylic acid (XII).

52 g of 2-methylamino-5-methyl-6-methylaminopyridine are added to a solution of 410 ml of 95% sulfuric acid in 100 ml of water and then mixture is heated for 48 hours at 100° C. After cooling, the reaction medium is poured over ice and neutralized with aqueous ammonia. The water is evaporated under vacuum and the residue is taken up in methanol. After filtration of the minerals, evaporation of the methanol provides 57 g of a brown solid mass which will be used in the next step without further purification.

Step 4: 2-Carboxamido-5-methyl-6-methylaminopyridine (XIII).

50 g of the solid obtained above are taken up in 1.5 l of ethanol supplemented with 38 ml of concentrated sulfuric acid. The mixture is heated at the reflux temperature of the solvent for 24 hours. After cooling, 1 liter of 32% aqueous ammonia is added and the mixture is heated for 4 hours at 50° C. The ethanol is evaporated and the residue supplemented with 100 ml of salt water is extracted 10 times with dichloromethane and then the organic phases are washed with N sodium hydroxide, dried over MgSO$_4$ and evaporated to dryness. The crystals are washed with ether and then dried to give 20.5 g of white crystals. m.p.=182° C.

Step 5: (6-Aminomethyl-5-methylpyridin-2-yl)methylamine (IVb)

11.9 g of 2-carboxamido-5-methyl-6-methylaminopyridine are dissolved in 60 ml of tetrahydrofuran. 143 ml of a 1 M lithium aluminum hydride solution in tetrahydrofuran are then slowly introduced. The solution is heated at the reflux temperature of the solvent for 4 hours, and then cooled on an ice bath. 5 ml of water are then introduced dropwise, followed by 3.75 ml of 20% sodium hydroxide and finally 35 ml of water. The white solid is separated by filtration and the organic phase is evaporated to dryness. The residue is chromatographed on silica 60 with a dichloromethane 90-methanol 9-aqueous ammonia 1 mixture to give 8.4 g of a yellow oil.

$^1$H NMR (DMSO-$d_6$): δ 7.12 (d, J=7.16 Hz, 1H)-6.42 (d, J=7.16 Hz, 1H)-5.80 (m, 1H)-3.62 (s, 2H)-2.82 (d, J=4.8 Hz, 3H)-1.99 (s, 3H)-1.5-2.1 (broad, 2H).

EXAMPLE 2

[1-(3-Chloro-4-fluorobenzoyl)-4-fluoro-piperidin-4-yl]hydroxyacetonitrile (III)

Step 1: 6-(3-Chloro-4-fluorobenzoyl)-1-oxa-6-azaspiro[2.5] octane-2-carbonitrile (V).

A suspension of 1-(3-chloro-4-fluorobenzoyl)piperidin-4-one (4160 g, 16.27 mol) in 28.4 liters of dichloromethane and 11.7 liters of sodium hydroxide at 30.5%, supplemented with 186 g of tetrabutylammonium chloride, is cooled to 15° C. Chloroacetonitrile (1540 ml, 24.4 mol) is then added slowly and with vigorous stirring and the mixture is stirred for 3 hours at 20° C. Further addition of chloroacetonitrile (500 ml) is carried out in order to complete the reaction. The reaction medium is diluted with dichloromethane (8.5 liters) and water (20 liters) and then separated by decantation and washed again with water. The brown solution obtained is decolorized with 2 kg of silica and 500 g of animal charcoal and then evaporated to dryness. The residue obtained is crystallized from isopropanol in order to give, after filtration, 3426 g of brown crystals. m.p.=100–101° C.

Step 2: [1-(3-Chloro-4-fluorobenzoyl)-4-fluoropiperidin-4-yl]hydroxyacetonitrile (III).

6-(3-Chloro-4-fluorobenzoyl)-1-oxa-6-azaspiro[2.5]-octane-2-carbonitrile (2620 g, 8.89 mol) dissolved in dichloromethane (6.6 liters) is introduced into a hastelloy reactor equipped with an appropriate gas washer (HF vapors). The solution is brought to 15° C. and 2.91 kg of the HF/pyridine complex at 70% are added and the medium is stirred for 6 hours at 40° C. The reaction medium is then washed twice with 10 liters of water and then with a $K_2CO_3$ solution and finally with water. The organic phase is evaporated under vacuum and the residue crystallized from 10 liters of isopropanol. The filtration and drying under vacuum of the precipitate provide 1540 g of white crystals. m.p.=139–140° C.

EXAMPLE 3

(3-Chloro-4-fluorophenyl)(4-fluoro-4-{[(5-methylpyridin-2-ylmethyl)amino]methyl}piperidin-1-yl)-methanone (Ia)

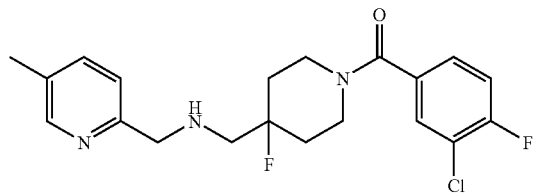

Introduce the [1-3-chloro-4-fluorobenzoyl)-4-piperidin-4-yl]hydroxyacetonitrile (5.3 g, 0.0169 mol), (5-methylpyridin-2-yl)methylamine (dihydrochloride) (3.6 g, 0.0185 mol), 1,4-diazabicyclo[2.2.2]octane (6.2 g, 0.055 mol), sodium cyanoborohydride (1.25 g, 0.02 mol) and 150 ml of methanol into a round-bottomed flask. The whole is stirred for 4 hours at room temperature, and then evaporated to dryness. The residue is taken up in sodium bicarbonate and extracted with ethyl acetate, the organic phases are washed with water and then dried over $MgSO_4$ and evaporated. The residue is chromatographed on silica 60 with a dichloromethane 95-methanol 4.5-aqueous ammonia 0.5 mixture to give 5.22 g of oil (78%). This oil is then treated in ethyl acetate with one equivalent of fumaric acid to give the white crystalline salt. m.p.=157° C.

MS: DCI>0 MH$^+$m/z=394. Elemental analysis: calculated: C, 56.53%, H 5.14%; N, 8.24%. found: C, 56.67%; H, 5.21%; N, 8.41%. $^1$H NMR (DMSOd$_6$): δ 10.4-9.4 (broad, 3H)-8.4 (dd, $^4$J=1.40 Hz-$^5$J=0.83 Hz, 1H)-7.7 (dd, $^4$J=7.18 Hz-$^4$J=1.93 Hz, 1H)-7.6 (dd, $^3$J=8 Hz, $^4$J=1.5 Hz, 1H)-7.50 (dd $^3$J=8.6 Hz, $^3$J=8.6 Hz, 1H)-7.45 (ddd, $^3$J=8.6 Hz, $^4$J=5 Hz, $^4$J=1.93 Hz, 1H)-7.35 (d $^3$J=8 Hz, 1H)-6.61 (s, 2H)-4.40-4.20 (broad, 1H)-3.92 (s, 2H)-3.50-3.30 (broad, 1H)-3.30-3.20 (broad, 1H)-3.15-2.95 (broad, 1H)-2.83 (d, $^3$J=20.7 Hz, 2H)-2.29 (s, 3H)-2.07-1.90 (broad, 1H)-1.90-1.80 (broad, 1H)-1.83-1.77 (m, 1H)-1.75-1.60 (m, 1H).

EXAMPLE 4

(3-Chloro-4-fluorophenyl)-4-fluoro-4-{[(5-methyl-6-methylaminopyridin-2-ylmethyl)amino]methyl}-piperidin-1-yl)methanone (Ib)

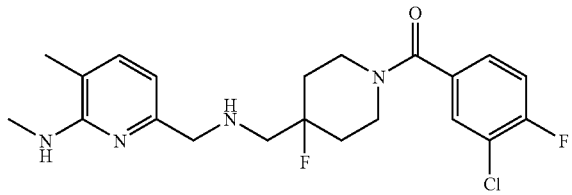

[1-(3-Chloro-4-fluorobenzoyl)-4-fluoropiperidin-4-yl]-hydroxyacetonitrile (11.6 g, 0.037 mol), (6-methyl-amino-5-methylpyridin-2-yl)methylamine (6.8 g, 0.045 mol), 1,4-diazabicyclo[2.2.2]octane (9.1 g, 0.081 mol), sodium cyanoborohydride (3.8 g, 0.06 mol), FeSO$_4$.7H$_2$O (11.3 g, 0.0407 mol) and 300 ml of methanol are introduced into a round-bottomed flask. The whole is stirred for 4 hours at room temperature and then evaporated to dryness. The residue is taken up in water and extracted 3 times with ethyl acetate, the organic phases are washed with water and then with salt water and dried over MgSO$_4$. The evaporation of the solvent gives an oil which is then chromatographed on silica 60 with dichloromethane 95-methanol 4.5-aqueous ammonia 0.5 to give 14.8 g of base (94%). Salification in ethyl acetate with one equivalent of glycolic acid gives a white crystalline salt.

m.p.=122° C. MS:ESI>0 MH$^+$ m/z=423. Elemental analysis:

calculated: C 55.37%-H, 5.86%-N, 11.23%. found: C, 55.17%; H, 5.99%; N, 11.08%. $^1$H NMR (D$_2$O): δ 7.61 (dd, $^4$J=2 Hz-$^4$J=7 Hz, 1H)-7.47 (d $^3$J=7.1 Hz, 1H)-7.45 (m, 1H)-7.39 (dd, $^3$J=8.6 Hz-$^3$J=8.6 Hz, 1H)-6.73 (d, $^3$J=7.2 Hz, 1H)-4.94 (s, HOD)-4.55-4.45 (d, $^2$J=11 Hz, 1H)-4.28 (s, 2H)-4.01 (s, 2H)-3.70-3.80 (d, $^2$J=11 Hz, 1H)-3.45-3.60 (dd, $^2$J=11 Hz-$^3$J=11 Hz, 1H)-3.35-3.25 (m, 1H)-3.35 (d, $^3$J=20.5

Hz, 2H)-3.03 (s, 3H)-2.30-2.15 (dd, $^2J=10$ Hz-$^3J=10$ Hz, 1H)-2.17 (s, 3H)-2.10-1.90 (m, 1H)-1.95-1.80 (m, 1H)-1.80-1.70 (m, 1H).

The invention claimed is:

1. A method for preparing pyridin-2-yl-methylamine derivatives of formula (I):

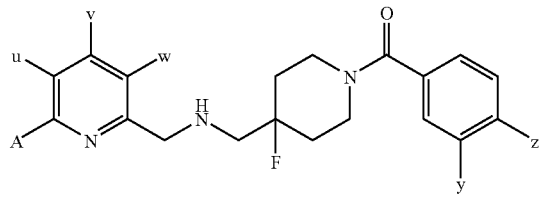

in which:
u represents a hydrogen atom or a methyl radical;
v represents a hydrogen atom or a chlorine atom or a methyl radical;
w represents a hydrogen atom or a fluorine atom or a methyl radical;
y represents a chlorine atom or a methyl radical;
z represents a hydrogen atom or a fluorine atom or a chlorine atom or a methyl radical; and
A represents:
   a hydrogen atom or a fluorine atom or a chlorine atom;
   a $C_1$–$C_5$ alkyl radical;
   a fluoroalkyl radical;
   a cyclopropyl radical;
   a 5-membered aromatic heterocyclic group;
   an alkoxy or alkylthio group;
   a cyclic amino group;
   an alkoxycarbonyl group; or
   an amino group of the type:

in which R2 or R3, which are identical or different, represent hydrogen, or a $C_1$–$C_5$ alkyl radical as defined above or a cyclopropyl or cyclobutyl radical or a trifluoromethyl radical,
comprising reacting a cyanohydrin of formula (III):

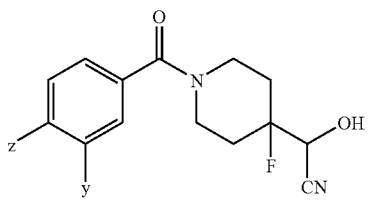

with a pyridin-2-ylmethylamines of formula (IV):

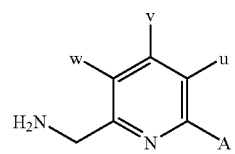

in which the radicals u, v, w, y, z and A have the meanings given above with respect to formula (I).

2. The method as claimed in claim 1, wherein the reaction is conducted in a reaction medium to which a simple or complex boron hydride is added to make the reaction medium reducing.

3. The method as claimed in claim 2, wherein the hydride is sodium cyanoborohydride.

4. The method as claimed in claim 1, wherein the reaction is conducted in the presence of a metal salt of iron, copper or zinc as a scavenger of cyanide ions.

5. The method as claimed in claim 4, wherein the metal salt is iron(II) sulfate, $FeSO_4.7H_2O$.

6. The method as claimed in claim 1, wherein the compound of formula (IV) is (5-methylpyridin-2-yl)methylamine of formula:

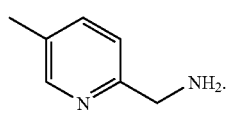

7. The method as claimed in claim 1, wherein the compound of formula (IV) is (6-methylamino-5-methylpyridin-2-yl)methylamine of formula:

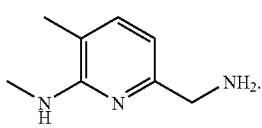

8. A method for preparing (6-methylamino-5-methylamino-2-yl)methylamine of formula (IVb), comprising converting 2-ethoxycarbonyl-5-methyl-6-pyridine of formula (IX) to 2-carboxamido-5-methy-6chloropyridine of formula (X) by means of aqueous ammonia:

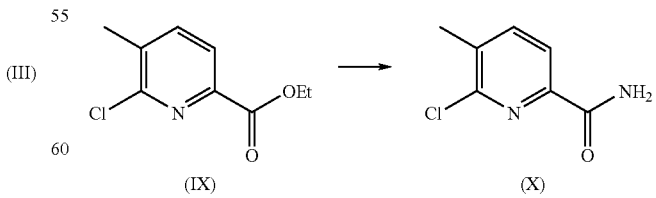

treating compound (X) with methylamine in solution and in the presence of $CuSO_4$ at high temperature and pressure to obtain 2-methylamido-5-methyl-6-methylaminopyridine of formula (XI):

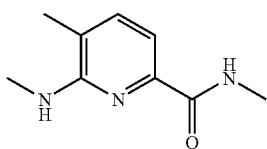
(XI)

subjecting compound (XI) to acid hydrolysis to form 5-methyl-6-methylaminopyridine-2-carboxylic acid of formula (XII):

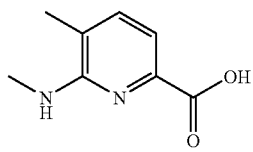
(XII)

converting compound (XII) to 2-carboxamido-5-methyl-6-methylaminopyridine of formula (XIII):

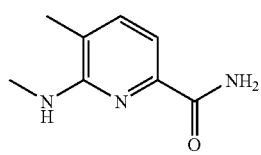
(XIII)

and, reducing compound (XIII) with lithium aluminum hydride to give (6-methylamino-5-pyridin-2-yl)methylamine of formula (IVb):

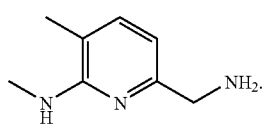
(IVb)

9. A method for preparing a (1-benzoyl-4-fluoropiperidin-4-yl)hydroxyacetonitriles of formula (III), comprising reacting an acetonitrile halide with a 1-benzoylpiperidin-4-one of formula II to give the corresponding cyanoepoxide of formula V:

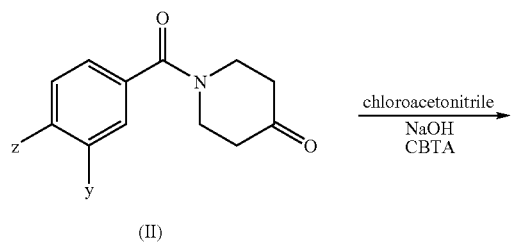
(II)

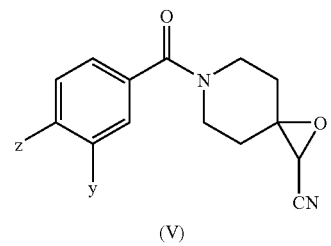
(V)

and, opening the cyanoepoxide of formula (V) with a fluorinating agent:

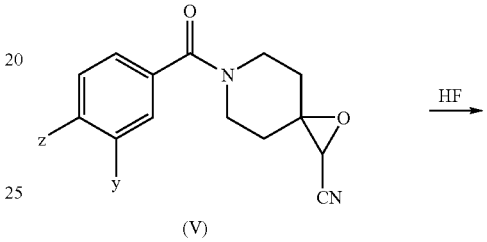
(V)

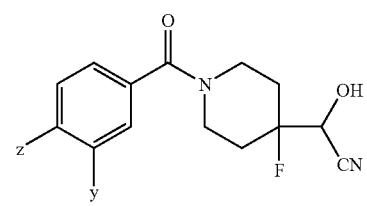
(III)

where y represents a chlorine atom or a methyl radical and z represents a hydrogen atom, a fluorine atom, a chlorine atom or a methyl radical.

10. The method as claimed in claim 9, wherein the acetonitrile halide is chloroacetonitrile and the fluorinating agent is a hydrogen fluoride-pyridine complex.

11. A synthesis intermediate of formula (III):

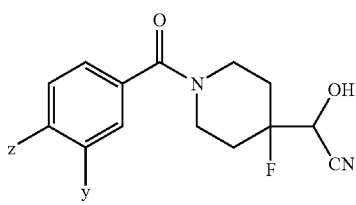
(III)

where y represents a chlorine atom or a methyl radical and z represents a hydrogen atom, a fluorine atom, a chlorine atom or a methyl radical.

* * * * *